United States Patent

Ban et al.

[11] Patent Number: 5,814,624
[45] Date of Patent: Sep. 29, 1998

[54] METHOD FOR OBTAINING ESTROGENS FROM PREGNANT MARE URINE BY SOLID-PHASE EXTRACTION

[75] Inventors: Ivan Ban, Hanover; Friederich Borchers, Laatzen; Henning Heinemann, Lehrte-Aligse; Heinz-Helmer Rasche, Burgdorf, all of Germany

[73] Assignee: Solvay Deutschland GmbH, Hanover, Germany

[21] Appl. No.: 933,089

[22] Filed: Sep. 18, 1997

Related U.S. Application Data

[63] Continuation of Ser. No. 799,812, Feb. 13, 1997, abandoned, which is a continuation of Ser. No. 623,396, Mar. 27, 1996, abandoned, which is a continuation of Ser. No. 372,164, Jan. 12, 1995, abandoned.

[30] Foreign Application Priority Data

Feb. 8, 1994 [DE] Germany .......................... 44 03 885.2
Oct. 26, 1994 [DE] Germany .......................... 44 38 273.1

[51] Int. Cl.$^6$ .................................................. A61K 35/22
[52] U.S. Cl. ........................ 514/170; 424/546; 119/174
[58] Field of Search ........................ 424/546; 514/120; 119/174

[56] References Cited

U.S. PATENT DOCUMENTS 3,769,401  10/1973  Thompson .............................. 424/100

*Primary Examiner*—Frederick Krass
*Attorney, Agent, or Firm*—Evenson, McKeown, Edwards & Lenahan, P.L.L.C.

[57] ABSTRACT

A method for obtaining an extract from urine of pregnant mares containing a natural mixture of conjugated estrogens by solid-phase extraction of the mixture of conjugated estrogens from the urine of pregnant mares on RP silica gel.

11 Claims, No Drawings

METHOD FOR OBTAINING ESTROGENS FROM PREGNANT MARE URINE BY SOLID-PHASE EXTRACTION

This application is a continuation of co-pending application Ser. No. 08/799,812, filed Feb. 13, 1997, now abandoned, which application is a continuation of application Ser. No. 08/623,396, filed Mar. 27, 1996, now abandoned, which application is a continuation of parent application Ser. No. 08/372,164, filed Jan. 12, 1995, now abandoned.

BACKGROUND OF THE INVENTION

The present invention relates to obtaining a natural mixture of conjugated estrogens from the urine of pregnant mares.

Estrogens are used in medicine for hormone replacement therapy. In particular, estrogen mixtures are used for the treatment and prophylaxis of the disorders of the climacteric period which occur in women after natural or artificial menopause. In this case, natural mixtures of conjugated estrogens such as are found in the urine of pregnant mares have proved particularly effective and well tolerated.

The dissolved solids content in the urine of pregnant mares (=pregnant mare urine or "PMU") may naturally vary within wide ranges, and may generally lie in a range of 40–90 g dry matter per liter. In addition to urea and other usual urine contents, phenolic constituents are contained in the solids content of the PMU in quantities of about 2–5% by weight relative to dry matter. These phenolic constituents include cresols and dihydro-3,4-bis[(3-hydroxyphenyl)methyl]-2(3H)-furanone, known as HPMF. These may be present in free or conjugated form. The PMU contains a natural mixture of estrogens which is largely present in conjugated form, e.g. as sulfuric acid semi-ester sodium salt (referred to hereinafter as "sulfate salt"). The content of conjugated estrogens (calculated as estrogen sulfate salt) may be between 0.3 and 1% by weight relative to dry matter.

Usually extracts containing conjugated estrogens are obtained from the PMU by extraction with a polar organic solvent which is immiscible, or only slightly miscible, with water, such as ethyl acetate, n-butanol or cyclohexanol. In such liquid—liquid extractions, however, a number of problems occur, such as severe foaming, sedimentation, emulsification and poor phase separation. Generally several extraction steps are required, which results in losses and only partial recovery of the estrogen content.

A solid-phase extraction of estrogens using a cartridge with silanised silica gel containing octadecylsilane radicals (Sep-Pak™ $C_{18}$ cartridge, manufactured by Waters Ass. Inc. Milford, Mass., USA) is proposed by Heikkinnen et al. (Clin. Chem. 27/7, (1981), 1186–1189) and by Shackleton et al. (Clinica Chimica Acta 107 (1980), 231–243) for treating small quantities of urine and plasma for analytical determination of estrogens by means of gas chromatography. In these reports, the estrogens are eluted from the cartridge with methanol. However, no details are given of the other substances contained in the estrogen-containing eluate.

Despite all the past activity in this field, there has remained a need in the art for a more effective way to recover estrogens from pregnant mare urine.

SUMMARY OF THE INVENTION

It is the object of the present invention to provide an industrial method for obtaining the natural mixture of conjugated estrogens from PMU, while avoiding the disadvantages known from the conventionally used liquid—liquid extractions, which method provides a product which is depleted in phenolic urine contents and is largely HPMF-free.

This and other objects of the invention are achieved by providing a method for obtaining a natural mixture, depleted in phenolic urine contents, of conjugated estrogens from pregnant mare urine, comprising the steps of a) treating a pregnant mare urine material with a quantity of a water-soluble base sufficient to establish a. pH value of at least 12, the mare urine material being selected from the group consisting of urine freed of mucilaginous substances and solids, a concentrate formed by reducing the volume of urine freed of mucilaginous substances and solids, and a urine retentate obtained by membrane filtration of urine freed of mucilaginous substances and solids; and then adding a sufficient quantity of an aqueous acid solution to adjust the treated urine material to a pH value in the range from 5 to 8.5; b) contacting the treated urine material from step a) having a pH of 5 to 8.5, with a quantity of a hydrophobized silica gel sufficient to adsorb conjugated estrogens contained therein, and separating a hydrophobized silica gel laden with a mixture of conjugated estrogens from a residual urine material; c) washing the estrogen-laden hydrophobized silica gel with an aqueous buffer solution having a pH of from 5 to 7, and d) contacting the washed hydrophobized silica gel with a quantity of an elution liquid sufficient to desorb the mixture of conjugated estrogens adsorbed thereon, the elution liquid comprising a mixture of water and a water-miscible organic solvent selected from the group consisting of water-miscible ethers, lower alkanols and lower aliphatic ketones, and recovering an eluate solution containing the mixture of conjugated estrogens.

DETAILED DESCRIPTION OF PREFERRED EMBODIMENTS

A method has now been discovered with which a mixture which is largely HPMF-free and which is depleted in phenolic urine contents, but contains the natural estrogen content of the PMU practically in its entirety can be obtained in a solid-phase extraction on hydrophobized silica gel, which mixture can be used as a starting material for the production of pharmaceuticals containing the natural mixture of conjugated estrogens from the PMU as active ingredient.

The method according to the invention for obtaining a natural mixture, depleted in phenolic urine contents, of conjugated estrogens from PMU is characterized in that a) a liquid urine material, which represents urine freed of mucilaginous substances and solids, a reduced concentrate of such urine or a reduced urine retentate obtained by ultrafiltration of such urine, is treated with a quantity of a water-soluble base sufficient to establish a pH value of at least 12, and then the pH value of the base-treated urine is adjusted to a pH value in the range from 5 to 8.5 by addition of a sufficient quantity of an aqueous acid solution, b) the urine which was pre-treated with the base and then adjusted to a pH of from 5 to 8.5 is contacted with a sufficient quantity of a hydrophobized silica gel to adsorb the mixture of conjugated estrogens contained in the urine, and a hydrophobized silica gel laden with the mixture of conjugated estrogens is separated from the rest of the urine, c) the hydrophobized silica gel laden with the mixture of conjugated estrogens is washed with an aqueous buffer solution having a pH in the range from 5 to 7, in particular 5, and d) the washed hydrophobized silica gel is contacted with a sufficient quantity of an elution liquid to desorb the mixture of conjugated estrogens adsorbed thereon, which liquid represents a mixture of water and a water-miscible organic solvent selected from the group consisting of water-miscible ethers, lower alkanols and lower aliphatic ketones, and an eluate containing the natural mixture of conjugated estrogens is separated from the hydrophobized silica gel and optionally reduced.

The PMU as such, a concentrate obtained therefrom by reduction or a retentate obtained therefrom by membrane filtration can be used for the method according to the invention. The collected urine is first freed of mucilaginous substances and solids in known manner. Advantageously, solids and mucilaginous substances are allowed to settle and these are then separated by known separation methods, for instance decanting, separation and/or filtration. Thus the PMU can for instance be passed through a known separating apparatus, e.g. a separator, a filtration unit or a sedimenter. A sand bed, for example, may serve as a separating apparatus, or commercially-available separators, e.g. nozzle separators or chamber separators, may be used. If desired, a microfiltration installation or an ultrafiltration installation may also be used, and if they are used it is possible to obtain a substantially bacteria-free and virus-free filtered PMU at the same time.

If desired, preservatives, germicides, bactericides and/or anthelmintics can be added to the urine.

If a concentrated PMU retentate is to be used instead of the PMU, this may be obtained from the PMU by known membrane filtration. The solids content of the retentate and the composition thereof may vary according to the PMU used and the membrane used for membrane filtration, for instance the pore width thereof, and the conditions of the filtration. For instance, when using a nanofiltration membrane, a practically loss-free concentration of the estrogen content in the PMU retentate can be achieved with simultaneous removal of up to 50% by weight of the lower-molecular PMU contents. PMU retertates which have been concentrated up to a ratio of approximately 1:10, for instance a ratio of about 1:7, and the volume of which can thus be reduced to approximately 1/10, for instance about 1/7, of the original PMU volume, can be used for the method according to the invention.

In method step a), a quantity of a water-soluble base sufficient to establish a pH value of at least 12, in particular 13 to 14, is added to the urine. Suitable water-soluble bases include inorganic or organic inert bases which are soluble in the urine and which are strong enough to achieve a pH value of at least 12. For instance, alkali metal or alkaline-earth metal hydroxides, in particular sodium hydroxide, or alternatively organic bases such as quaternary lower-alkylammonium hydroxides, are suitable. Preferably the base is added in the form of an aqueous solution containing at least 20% by weight of the base, preferably 40 to 60% by weight. A 45–55% aqueous sodium hydroxide solution has proved particularly advantageous. This alkaline preliminary treatment adjusts the pH value of the urine to at least 12, for instance a range of 12 to 14, preferably approximately 13, and this alkaline pH value is maintained for a period sufficient for cleavage of lactone groups contained in urine ingredients, which may generally be ½ to 2 hours. The treatment conditions must be selected such that the conjugated estrogens are not attacked. Thus the treatment prefer- ably takes place at room temperature and the amount of base added is restricted to the quantity required to achieve the desired pH value in the range of 12 to 14. The quantity of base required to achieve a pH value in the range of 12 to 14 may vary depending on the composition of the PMU used. When using 50% sodium hydroxide solution, generally quantities of about 100 to 700 ml 50% sodium hydroxide solution relative to 10 liters of PMU prove sufficient. Then the urine is adjusted to a pH value in the range of 5 to 8.5, preferably 7 to 8.5, in particular 8 to 8.5, by addition of an aqueous acid solution. Suitable acids include inert inorganic or organic acids which are soluble in the urine, such as hydrochloric acid, sulfuric acid, phosphoric acid or lower carboxylic acids such as acetic acid. For example, a concentrated aqueous hydrochloric acid solution has proved advantageous. The quantity of acid required to achieve the aforementioned pH range may vary according to the composition of the PMU used and the quantity of base used to render it alkaline. When using concentrated hydrochloric acid solution, the desired pH value can generally be achieved by addition of approximately 25 to 100 g concentrated hydrochloric acid solution relative to 1 liter of PMU.

The hydrophobized silica gels which can be used in method step b) are known reverse-phase silica gels (hereinafter "RP silica gels"), that is to say, chemically modified silica gels which carry hydrophobic functional groups or ligands. For instance, silanised RP silica gels which contain n-octadecyldimethylsilyloxy, n-octyldimethylsilyloxy or dimethylhydroxysilyloxy radicals as hydrophobic functional groups are suitable. For instance, silanised silica gels having average grain sizes of 15 to 500 μm are suitable. Silica gel containing dimethylhydroxylsilyloxy radicals and having an average grain size in the range of 0.05–0.3 mm have proved particularly advantageous, for example, "Kieselgel 60/dimethylsilane derivative", manufactured by Merck.

According to the invention, the adsorption of the conjugated estrogens on the hydrophobized silica gel can be effected by contacting the optionally concentrated PMU or the retentate thereof with the hydrophobized silica gel, in that the urine pre-treated in method step a) is introduced into a reactor containing the silica gel and is maintained in contact with the silica gel therein for a sufficient time for adsorption of the estrogen content. Once adsorption of the conjugated estrogens on the hydrophobized silica gel has taken place, the silica gel laden with the mixture of conjugated estrogens can be separated from the rest of the urine in known manner. Advantageously, the urine can be passed through a column containing the silica gel at such a flow rate that the contact time is sufficient for adsorption of the estrogen content. For example, flow rates are suitable which correspond to a throughput of 5 to 20 parts by volume of PMU per one part by volume of silica gel per hour. The adsorption is preferably effected at room temperature. Advantageously, the rate of flow of the urine through the reactor can be controlled by operating at a slight overpressure or underpressure (relative to ambient pressure) The quantity of hydrophobized silica gel to be used may vary depending on the type of silica gel used and the quantity of solids contained in the urine pre-treated in method step a). When using pre-treated PMU, for instance one part by volume hydrophobized silica gel can be loaded with up to 80 parts by volume of pre-treated PMU without perceptible quantities of estrogen being detectable in the urine effluent. When using a pre-treated PMU concentrate or PMU retentate, the loading capacity of the hydrophobized silica gel is of course reduced to the extent at which it is concentrated. For instance, 1 part by volume hydrophobized silica gel may be laden with a quantity of urine corresponding to 30 to 80, preferably 40 to 50, parts by volume PMU.

The hydrophobized silica gel laden with the mixture of conjugated estrogens is washed in method step c) with an aqueous buffer solution having a pH in the range from 5 to 7, preferably about 5. Preferably an aqueous acetic acid/ acetate buffer solution adjusted to about pH 5 is used as the washing liquid. In particular 0.1 to 1-molar, preferably 0.1 to 0.2-molar, acetic acid/acetate buffer solutions are suitable. The quantity of washing liquid is selected such that it is sufficient largely to wash out phenolic urine contents, without significant quantities of conjugated estrogens being washed out with them. For instance, the use of 8 to 15, in particular 9 to 10, bed volumes washing liquid per bed volume hydrophobized silica gel has proved advantageous. In this case, the washing liquid is advantageously passed through a reactor containing the hydrophobized silica gel at a flow rate of 5 to 20 parts by volume of washing liquid per one part by volume of silica gel per hour.

In method step d), the washed hydrophobized silica gel laden or charged with the mixture of conjugated estrogens is then treated with a quantity of an elution liquid sufficient to elute the mixture of conjugated estrogens, and an eluate containing the natural mixture of conjugated estrogens of the PMU is obtained. The elution liquid used according to the invention represents a mixture of water and a water-miscible ether, lower alkanol and/or lower aliphatic ketone. Suitable ether constituents of the elution liquid include water-miscible cyclic ethers such as tetrahydrofuran or dioxane, but also water-miscible open-chain ethers such as ethylene glycol dimethyl ether (=monoglyme), diethylene glycol dimethyl ether (=diglyme) or ethyloxyethyloxy ethanol (=Carbitol). Suitable lower alkanols include water-miscible alkyl alcohols with 1 to 4, preferably 1 to 3, carbon atoms, in particular ethanol or isopropanol. Suitable lower aliphatic ketones include water-miscible ketones with 3 to 5 carbon atoms, in particular acetone. Elution liquids in which the organic solvent is ethanol have proved particularly advantageous. In the elution liquid there may be a volume ratio of water-miscible organic solvent to water in the range from 40:60 to 20:80, preferably approximately 30:70. The quantity of eluent used may be approximately 3 to 5 bed volumes per bed volume hydrophobized silica gel. Advantageously, the elution liquid is passed through a vessel or reactor containing the hydrophobized silica gel laden with the estrogen mixture at such a flow rate that the contact time is sufficient to completely elute the mixture of conjugated estrogens. When using a mixture of tetrahydrofuran and/or ethanol with water in a volume ratio of 30:70, for instance flow rates of 5 to 20 parts by volume of elution liquid per one part by volume of silica gel per hour are suitable. Advantageously, the flow rate is regulated by operating at slightly elevated pressure, e.g. at an overpressure of up to 0.2 bar (relative to ambient pressure), and the eluate is collected in several fractions. The contents of conjugated estrogens and phenolic urine ingredients such as cresols and HPMF in the individual eluate fractions may be determined in known manner by high-performance liquid chromatography ("HPLC").

Upon elution, initially a slightly-colored to colorless, practically estrogen-free preliminary fraction is obtained, the quantity of which corresponds generally to approximately one bed volume. The bulk of the conjugated estrogens, for instance between 80 and 99% of the conjugated estrogens present in the starting PMU, is in the subsequent dark-yellow/brown colored main eluate fractions, the quantity of which is generally 1 to 2 bed volumes. Generally only traces of conjugated estrogens are contained in the following final fractions. If succeeding fractions are obtained which still have a content of conjugated estrogens of above 10% by weight relative to dry matter and less than 0.6% by weight relative to dry matter of cresols and HPMF, these may be combined with the estrogen-rich main eluate for further processing.

The main eluate separated from the silica gel in the manner previously described contains the natural mixture of conjugated estrogens occurring in the PMU in addition to only a small proportion of the content of phenolic urine ingredients originally present in the PMU. This eluate may be used as a starting material for the production of medicaments containing the natural mixture of conjugated estrogens. If desired, the eluate may be further reduced in volume in known manner, in order to obtain a concentrate substantially freed of organic solvent which is suitable for further galenic processing. If desired, an eluent-free solids mixture can also be produced by spray-drying. If the natural mixture of conjugated estrogens is to be used for the production of solid medicaments, it may be advantageous to admix a solid carrier substance with the eluate containing the conjugated estrogens before concentration or spray-drying, in order to obtain in this manner a solids mixture containing the conjugated estrogens and carrier substances. Both the eluate containing the estrogen mixture and a concentrate produced therefrom or spray-dried solids product may be processed in known manner into solid or liquid galenic preparations such as tablets, dragees, capsules or emulsions. These galenic preparations can be produced according to known methods using conventional solid or liquid carrier substances such as starch, cellulose, lactose or talcum, or liquid paraffins and/or using conventional pharmaceutical adjuvants, such as tablet disintegrating agents, solubilizers or preservatives. For instance, the product containing the conjugated estrogens may be mixed with the pharmaceutical carrier substances and auxiliaries in known manner and the mixture converted into a suitable dosage form.

The following examples are intended to illustrate the invention in further detail without restricting its scope.

EXAMPLES 1–5

General operating procedure for obtaining an extract from PMU which is largely depleted in phenolic urine contents and which contains the natural mixture of conjugated estrogens contained in the PMU.

A) Preliminary treatment of the PMU.

10 liters of a PMU filtered through a sand bed 5 cm high or through a microfiltration apparatus (for dry matter (DM) content and also the contents of estrone sulfate salt, cresol and HPMF as determined by HPLC see following table of examples) were adjusted to pH 13 by adding a 50% aqueous sodium hydroxide solution (density at 20° C.=1.52 g/ml) with vigorous stirring (for quantity of NaOH solution added see table of examples) and then were stirred for one hour at room temperature. The resulting alkaline urine was adjusted to a pH value of 8 to 8.5 by adding a concentrated aqueous hydrochloric acid solution (approximately 35%).

B) Adsorption of PMU estrogen content on RP silica gel.

A column having a height of 50 cm and a diameter of 5 cm was filled with 100 g (=a volume of approximately 193 ml≈1 bed volume) of RP silica gel (="Kieselgel 60/Dimethylsilane derivative", manufactured by Merck, Order No. 7719, grain size 63 to 200 $\mu$m). The column was first washed with 0.5 liter of water, then with 0.25 liter of methanol and once again with 0.5 liter of water.

Urine material, which had been pre-treated as described in step A), was passed through the column at an overpressure (relative to ambient pressure) of 0.2 bar and at a flow rate of 60 ml/minute. The estrogen content of the PMU was fully adsorbed on the RP silica gel column. The urine effluent was analyzed by HPLC to determine its estrone sulfate salt content and proved to be practically estrogen-free. The bottom product was discarded.

C) Washing of the estrogen-laden RP silica gel column.

The charged silica gel column was washed with 2 liters (=approximately 10 bed volumes) of a 0.15-molar acetic acid/sodium acetate buffer solution. The buffer solution was produced by adding solid sodium acetate (approximately 107 g) to a 0.15-molar aqueous acetic acid solution until pH 5 was reached. The washing liquid effluent was analyzed by HPLC to determine its contents of estrone sulfate salt, cresol and HPMF, and was found to contain less than 5% of the estrogen content of the starting PMU.

following table of examples. This fraction represents an extract suitable for further galenic processing.

E) Regeneration of the RP silica gel column.

The column was regenerated by initially washing it with 2 liters of water, then with 0.5 liter of methanol and again with 2 liters of water. Then the column can be reused for the process. The column can be regenerated and re-used many times, for instance up to ten times.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

| Example No. | | 1 | 2 | 3 | 4 | 5 |
|---|---|---|---|---|---|---|
| Starting PMU | | | | | | |
| Weight percent dry matter (DM) | | 6.0 | 7.3 | 7.3 | 7.7 | 7.7 |
| mg Estrogen sulf. salt content | (≈wt-% DM) | 860.0 (0.14) | 1040 (0.14) | 1090 (0.15) | 1250 (0.16) | 1250 (0.16) |
| mg Cresol content | (≈wt-% DM) | 10170.0 (1.70) | 2220 (0.30) | 2410 (0.33) | 2940 (0.38) | 2940 (0.38) |
| mg HPMF content | (≈wt-% DM) | 680.0 (0.11) | 840 (0.12) | 830 (0.11) | 890 (0.12) | 890 (0.12) |
| Pretreatment | | | | | | |
| g 50% NaOH solution added (pH) | | 629 (13) | 250 (13) | 252 (13) | 291 (13) | 305 (13) |
| g conc. HCl solution added (pH) | | 767 (8.5) | 284 (8.5) | 263 (8.0) | 334 (7.9) | 347 (8.0) |
| Elution Liquid | | Tetrahydrofuran/-Water 30:70 | Ethanol/Water 30:70 | Isopropanol/-Water 30:70 | Monoglyme/Water 30:70 | Acetone/Water 30:70 |
| Eluate Fraction 2 | | | | | Eluate Fractions | |
| Weight percent dry matter (DM) | | 3.1 | 1.8 | | 2 and 3 | |
| mg Estrogon sulf. salt content | (≈wt-% DM) | 858.2 (13.84) | 852 (23.7) | 894.2 (21.3) | 1045.1 (19.97) | 971.9 (20.9) |
| mg Cresol content | (≈wt-% DM) | 18.0 (0.29) | 7.4 (0.21) | 10.9 (0.26) | 33.7 (0.46) | 14.7 (0.32) |
| mg HPMF content | (≈wt-% DM) | 6.4 (0.10) | 9.2 (0.26) | 10.7 (0.25) | 7.3 (0.14) | 0 (0.0) |

D) Desorption of conjugated estrogens from washed RP silica gel column and isolation of an estrogen-rich eluate fraction.

One liter of the elution liquid (water/solvent mixture, for composition see following table of examples) was passed through the column at an overpressure of 0.2 bar (relative to ambient pressure) and at a flow rate of approximately 60 ml/min. The eluate effluent was collected in several fractions (each having a volume of approximately 200 ml=approximately 1 bed volume). The individual fractions were analyzed by HPLC to determine their respective contents of estrone sulfate salt, cresol and HPMF. The initial fraction was collected for as long as the eluate appeared colorless to slightly yellowish in color. The volume of this fraction was 150 to 200 ml. This fraction contained only traces of estrogen sulfate salt.

As soon as the color of the eluate changed to an intense dark-yellow/brown color, the next fraction of approximately 200 ml was collected. This fraction contained approximately 80 to 98% of the total quantity of conjugated estrogens charged on the column. The remaining fractions contained only small quantities of estrogen sulfate salt. If desired, the remaining fractions can be recycled to method step B) after first distilling off the solvent content.

The dry matter content in % by weight and the respective contents of estrone sulfate salt, cresol and HPMF as determined by HPLC in the second fraction, which contained the majority of the conjugated estrogens, are listed in the

What is claimed is:

1. A method for obtaining a natural mixture, depleted in phenolic urine contents, of conjugated estrogens from pregnant mare urine, said method comprising the steps of:

a) treating a pregnant mare urine material with a quantity of a water-soluble base sufficient to establish a pH value of at least 12, said mare urine material being selected from the group consisting of urine freed of mucilaginous substances and solids, a concentrate formed by reducing the volume of urine freed of mucilaginous substances and solids, and a urine retentate obtained by membrane filtration of urine freed of mucilaginous substances and solids; and then adding a sufficient quantity of an aqueous acid solution to adjust the treated urine material to a pH value in the range from 5 to 8.5;

b) contacting the treated urine material from step a) having a pH of 5 to 8.5, with a quantity of a hydrophobized silica gel sufficient to adsorb conjugated estrogens contained therein, and separating a hydrophobized silica gel laden with a mixture of conjugated estrogens from a residual urine material;

c) washing the estrogen-laden hydrophobized silica gel with an aqueous buffer solution having a pH of from 5 to 7, and d) contacting the washed hydrophobized silica gel with a quantity of an elution liquid sufficient to desorb the mixture of conjugated estrogens adsorbed thereon, said elution liquid comprising a mixture of water and a water-miscible organic solvent selected from the group consisting of water-miscible ethers, lower alkanols and lower aliphatic ketones, and recovering an eluate solution containing said mixture of conjugated estrogens.

2. A method according to claim 1, further comprising reducing the volume of said eluate to obtain a more concentrated eluate solution.

3. A method according to claim 1, wherein in step a) the urine material is mixed with the base and thereafter maintained at a pH of at least 12 for a period of time sufficient to cleave any lactone groups in substances contained in the urine material.

4. A method according to claim 1, wherein in step a) the urine material is treated with said water-soluble base by mixing the urine material with an aqueous solution of the water-soluble base.

5. A method according to claim 1, wherein said hydrophobized silica gel is a silanised silica gel bearing dimethylhydroxysilyloxy radicals.

6. A method according to claim 1, wherein in step b) one part by volume of hydrophobized silica gel is contacted with an amount of urine material corresponding to from 30 to 80 parts by volume of pregnant mare urine.

7. A method according to claim 6, wherein one part by volume of hydrophobized silica gel is contacted with an amount of urine material corresponding to from 40 to 50 parts by volume of pregnant mare urine.

8. A method according to claim 1, wherein step b) is carried out by passing the urine material through a vessel containing the hydrophobized silica gel at a flow rate corresponding to from 5 to 20 parts by volume of urine per one part by volume of hydrophobized silica gel per hour.

9. A method according to claim 1, wherein in step c) the aqueous buffer solution is an aqueous acetic acid/acetate buffer solution having a pH of about pH 5.

10. A method according to claim 1, wherein in step d) the elution liquid is a mixture of water and a water-miscible organic solvent having a volume ratio of organic solvent to water in the range from 20:80 to 40:60.

11. A method according to claim 10, wherein the elution liquid comprises a 30:70 volume ratio of water-miscible organic solvent to water.

\* \* \* \* \*